(12) United States Patent
Palanker et al.

(10) Patent No.: US 7,047,080 B2
(45) Date of Patent: May 16, 2006

(54) SELF-SUFFICIENT RETINAL PROSTHESIS POWERED BY INTRAOCULAR PHOTOVOLTAIC CELLS

(75) Inventors: Daniel V. Palanker, Sunnyvale, CA (US); Alexander Vankov, Mountain View, CA (US); Mark Blumenkranz, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 165 days.

(21) Appl. No.: 10/741,941

(22) Filed: Dec. 19, 2003

(65) Prior Publication Data

US 2004/0181265 A1    Sep. 16, 2004

Related U.S. Application Data

(60) Provisional application No. 60/447,647, filed on Feb. 14, 2003.

(51) Int. Cl.
*A61N 1/18*     (2006.01)
*A61F 2/14*     (2006.01)

(52) U.S. Cl. .............. 607/54; 607/53; 623/4.1
(58) Field of Classification Search .......... 607/53, 607/54, 141, 148; 623/4.1
See application file for complete search history.

(56) References Cited

U.S. PATENT DOCUMENTS

| | | | | |
|---|---|---|---|---|
| 4,628,933 A | | 12/1986 | Michelson | 128/419 |
| 5,024,223 A | * | 6/1991 | Chow | 607/53 |
| 5,109,844 A | * | 5/1992 | de Juan et al. | 607/53 |
| 5,411,540 A | | 5/1995 | Edell et al. | 607/53 |
| 5,556,423 A | | 9/1996 | Chow et al. | 607/54 |
| 5,865,839 A | * | 2/1999 | Doorish | 623/6.63 |
| 6,298,270 B1 | | 10/2001 | Nisch et al. | 607/54 |
| 6,324,429 B1 | | 11/2001 | Shire et al. | 607/54 |
| 6,427,087 B1 | | 7/2002 | Chow et al. | 607/54 |
| 6,647,297 B1 | | 11/2003 | Scribner | 607/54 |
| 6,804,560 B1 | * | 10/2004 | Nisch et al. | 607/54 |
| 2005/0049578 A1 | * | 3/2005 | Tu et al. | 604/890.1 |

OTHER PUBLICATIONS

Palanker et al., "Can A Self-Powered Retinal Prosthesis Support 100,000 Pixels in the Macula?" Investigative Ophthalmology & Visual Science 2003; 44: E-Abstract 5067.

* cited by examiner

*Primary Examiner*—Jeffrey R. Jastrzab
*Assistant Examiner*—John D. Alexander
(74) *Attorney, Agent, or Firm*—Lumen Intellectual Property Services, Inc.

(57) ABSTRACT

A self-sufficient retinal prosthesis powered by intra-ocular photovoltaic cells illuminated only by ambient light is provided. Photovoltaic cells can be disposed at the periphery of the retina or in the anterior chamber of the eye. An adaptive retinal prosthesis is also provided, such that the number of pixels energized in the prosthesis is selected according to the variable available power from ambient light.

19 Claims, 5 Drawing Sheets

SELF-SUFFICIENT RETINAL PROSTHESIS POWERED BY INTRAOCULAR PHOTOVOLTAIC CELLS

CROSS REFERENCE TO RELATED APPLICATIONS

This application claims priority from U.S. provisional application 60/447,647 filed on Feb. 14, 2003, which is hereby incorporated by reference.

FIELD OF THE INVENTION

The present invention relates generally to neural prostheses. More particularly, the present invention relates to providing electrical power to a retinal prosthesis.

BACKGROUND

A leading cause of blindness in developed countries is Age-related Macular Degeneration (AMD). AMD is a disease which degrades the photoreceptors (i.e., rods and cones) in the retina, but generally does not degrade other parts of the retina. Accordingly, one approach for treating AMD (and other conditions, such as retinitis pigmentosa, that also primarily degrade the photoreceptors) is to implant a retinal prosthesis providing the same functionality as healthy photoreceptors (i.e., selective stimulation of neural tissue in the retina responsive to visual inputs).

Such a retinal prosthesis performs the functions of 1) receiving a visual image and 2) selectively stimulating retinal neural tissue responsive to the received visual image. In many cases, both of these functions are performed electrically, since electrical detection of optical signals and electrical excitation of neural cells are both known. However, a known problem in the art is providing sufficient electrical power to such a prosthesis, as the following example will make clear.

An electrode for stimulating a neural cell typically has a radius $r_o$ of about 5 µm. The impedance between an electrode of radius $r_o$ and a (hypothetical) large electrode at infinity in a medium having resistivity $\gamma$ is given by $R=\gamma/(2\pi r_o)$. For this example, we assume a resistivity $\gamma=70$ $\Omega$cm, which is the resistivity of a typical saline solution and is thus representative of the resistivity to be expected in vivo. Thus the resistance R seen by the electrode of this example is 22 k$\Omega$.

The electrode potential U (relative to infinity) required to establish a potential drop $\Delta U$ across a cell of length L in contact with the electrode is given by $U=\Delta U(r_o+L)/L$. Assuming a cell length $L=10$ µm, and a typical cell depolarization voltage of 30 mV, a potential $U=45$ mV and current $I=2$ µA is required on the electrode to depolarize the cell in this example. The power dissipation $P=I^2R=U^2/R$ in this example is about 0.35 µW while the current is flowing. As the electrode size $r_o$ increases, the required power increases because R decreases and U increases for fixed $\Delta U$.

The power flux of ambient light on the retina is typically about 0.9 µW/mm$^2$ outdoors on a sunny day. The conversion efficiency of optical power to electrical power provided by photovoltaic cells is on the order of 30%, so the available electrical power at the retina is roughly 0.3 µW/mm$^2$. The area of the macula is about 9 mm$^2$, so a retinal prosthesis powered by a macula-sized photocell would only have enough power to drive about 8 electrodes, which is far fewer electrodes than what is needed to provide reasonable vision for a patient.

For this reason, power is typically supplied to an electrical retinal prosthesis externally. Known methods for accomplishing this include wireless transmission of radio-frequency (RF) power to an RF receiver incorporated into the intra-ocular portion of the prosthesis, and transmission of optical power to an intra-ocular photovoltaic cell connected to the prosthesis. The source for optical power transmission is typically a laser attached to glasses or goggles worn by a patient. Examples of such approaches are given in U.S. Pat. No. 6,324,429 to Shire et al., U.S. Pat. No. 6,298,270 to Nisch et al., and U.S. Pat. No. 4,628,933 to Michelson. In some of these prior art approaches, the external unit of the retinal prosthesis provides both electrical power and electrical image data to the intra-ocular unit of the prosthesis. In other cases, the external unit only provides power, and the intra-ocular unit converts the optical image to electrical form to drive neural cells in the retina. In either case, such prior art retinal prostheses require an external unit to at least provide power to the intra-ocular unit.

Accordingly, there is a need for a fully autonomous electrical retinal prosthesis requiring no external unit, which is not met by prior art approaches.

SUMMARY

The present invention provides a self-sufficient retinal prosthesis powered by intra-ocular photovoltaic cells illuminated only by ambient light. In one embodiment of the invention, photovoltaic cells are disposed at the periphery of the retina. In another embodiment of the invention, at least one photovoltaic cell is disposed in the anterior chamber of the eye. In still another embodiment of the invention, an adaptive retinal prosthesis is provided, such that the number of pixels energized in the prosthesis is selected according to the variable available power from ambient light. An advantage of the present invention is provision of a self-sufficient intra-ocular retinal prosthesis requiring no external unit to provide either power or image data to the intra-ocular unit.

DETAILED DESCRIPTION

Figure 1:
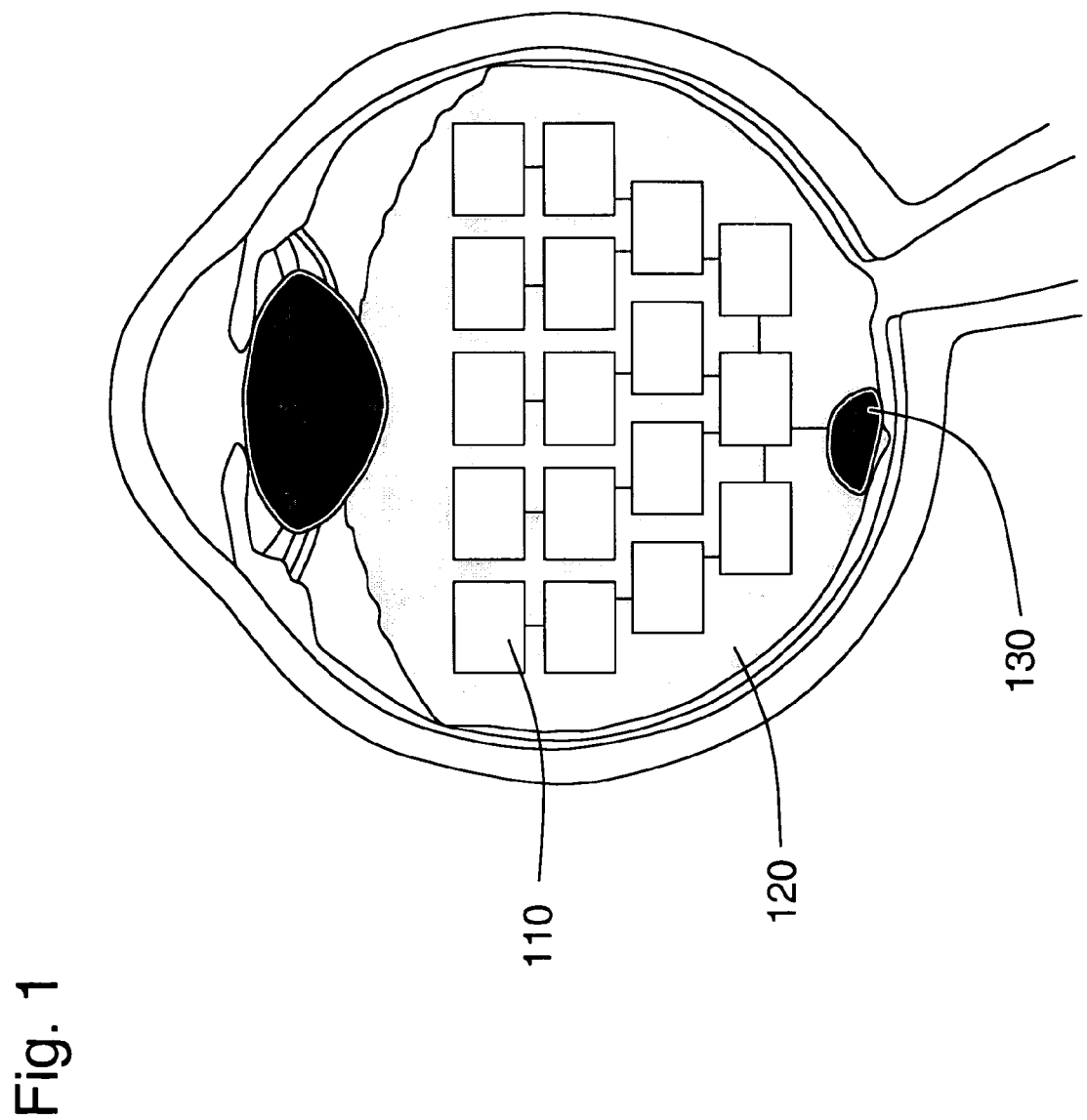
FIG. 1 shows an embodiment of the invention having photovoltaic cells disposed on the periphery of the retina.

FIG. 1 shows an embodiment of the invention disposed within an eye having a retina 120. A stimulating array 130 is preferably disposed at a central region of retina 120, as shown. Photovoltaic cells 110 are disposed at retina 120, preferably outside the macular region of retina 120. Photovoltaic cells 110 receive only ambient light and provide electrical power responsive to the ambient light. Here ambient light excludes light from a source for providing power to retinal prostheses, but includes all other light. Photovoltaic cells 110 are electrically connected to each other and to stimulating array 130 such that power provided by photovoltaic cells 110 is available at stimulating array 130. Such connections can be made in any convenient manner, and the invention is not limited to the particular arrangement shown on FIG. 1. Photovoltaic cells 110 can be disposed epiretinally or subretinally. Likewise, stimulating array 130 can be disposed epiretinally or subretinally.

Photovoltaic cells 110 can cover a hemisphere in the posterior pole of the eye. Assuming an inner diameter of the eye of 17 mm, the surface area of a corresponding hemisphere is 907 mm$^2$. Such a surface (if uniformly illuminated) can provide about 270 µW of electrical power, sufficient to power roughly 770 pixels based on the above example. In order to allow for some peripheral vision, photovoltaic cells 110 can be separated from each other, as shown on FIG. 1, to avoid completely covering the peripheral region of retina 120.

Figure 2:
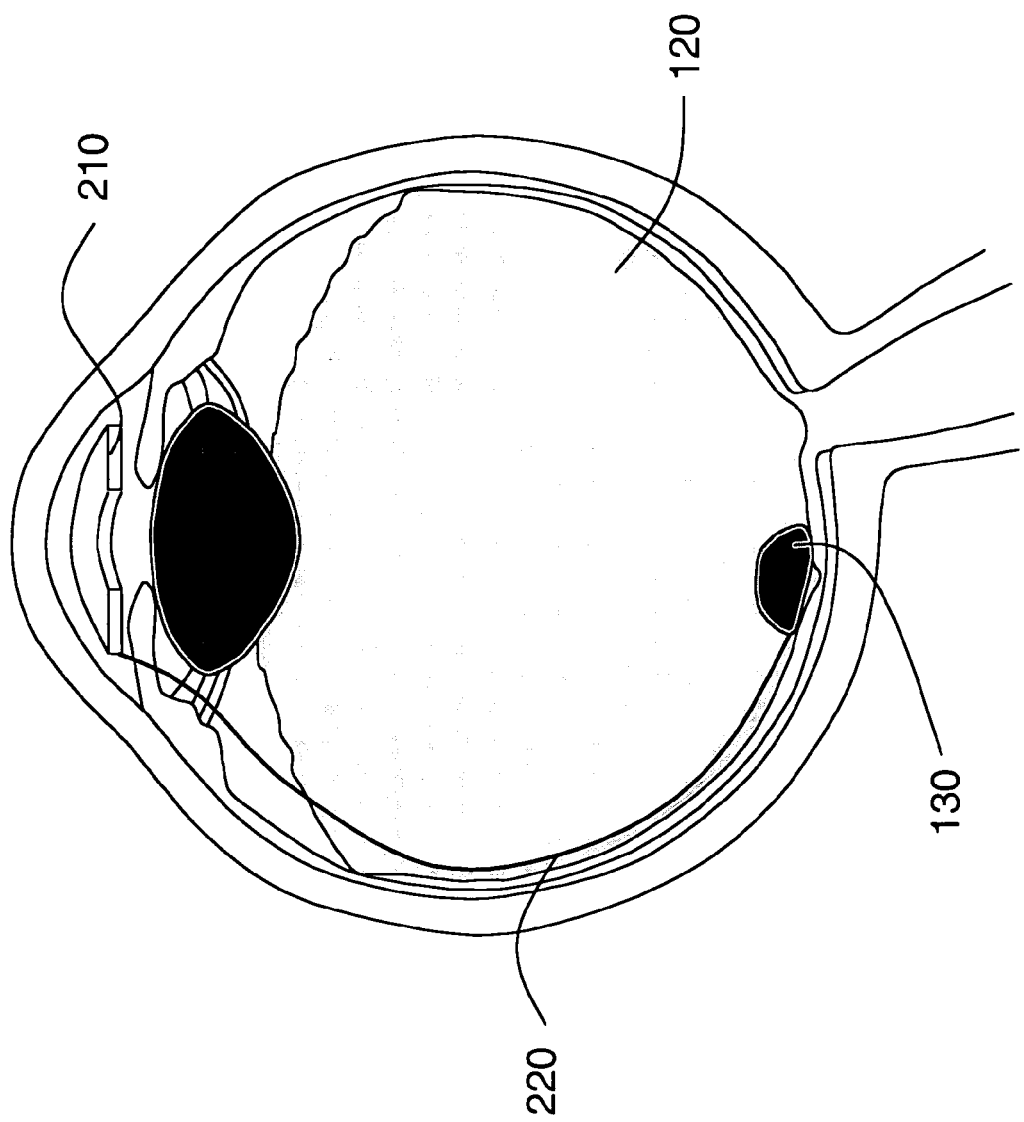
FIG. 2 shows an embodiment of the invention having a photovoltaic cell (or cell array) disposed in the anterior chamber of the eye.

FIG. 2 shows an embodiment of the invention having at least one photovoltaic cell 210 in the anterior chamber of the eye. Photovoltaic cell 210 is electrically connected to stimulating array 130 via a wire 220. The invention is not limited to the particular path for wire 220 between photovoltaic cell 210 and stimulating array 130 shown on FIG. 2. The arrangement of FIG. 2 can provide significantly more electrical power than the arrangement of FIG. 1, because the area of photovoltaic cell (or cells) 210 can be made significantly larger than the area of the pupil of the eye. For example, if the area of photocell(s) 210 is that of a 1 cm diameter circle, and the pupil diameter is 2 mm, 25 times as much light hits photocell(s) 210 as passes through the pupil. Continuing the example from the discussion of FIG. 1, roughly 6.75 mW of electrical power would be available in the arrangement of FIG. 2, sufficient to power roughly 19000 pixels. Photovoltaic cell (or cells) 210 can also be positioned elsewhere within the eye (e.g., within the cornea of the eye via an intrastromal implant).

Figure 3:
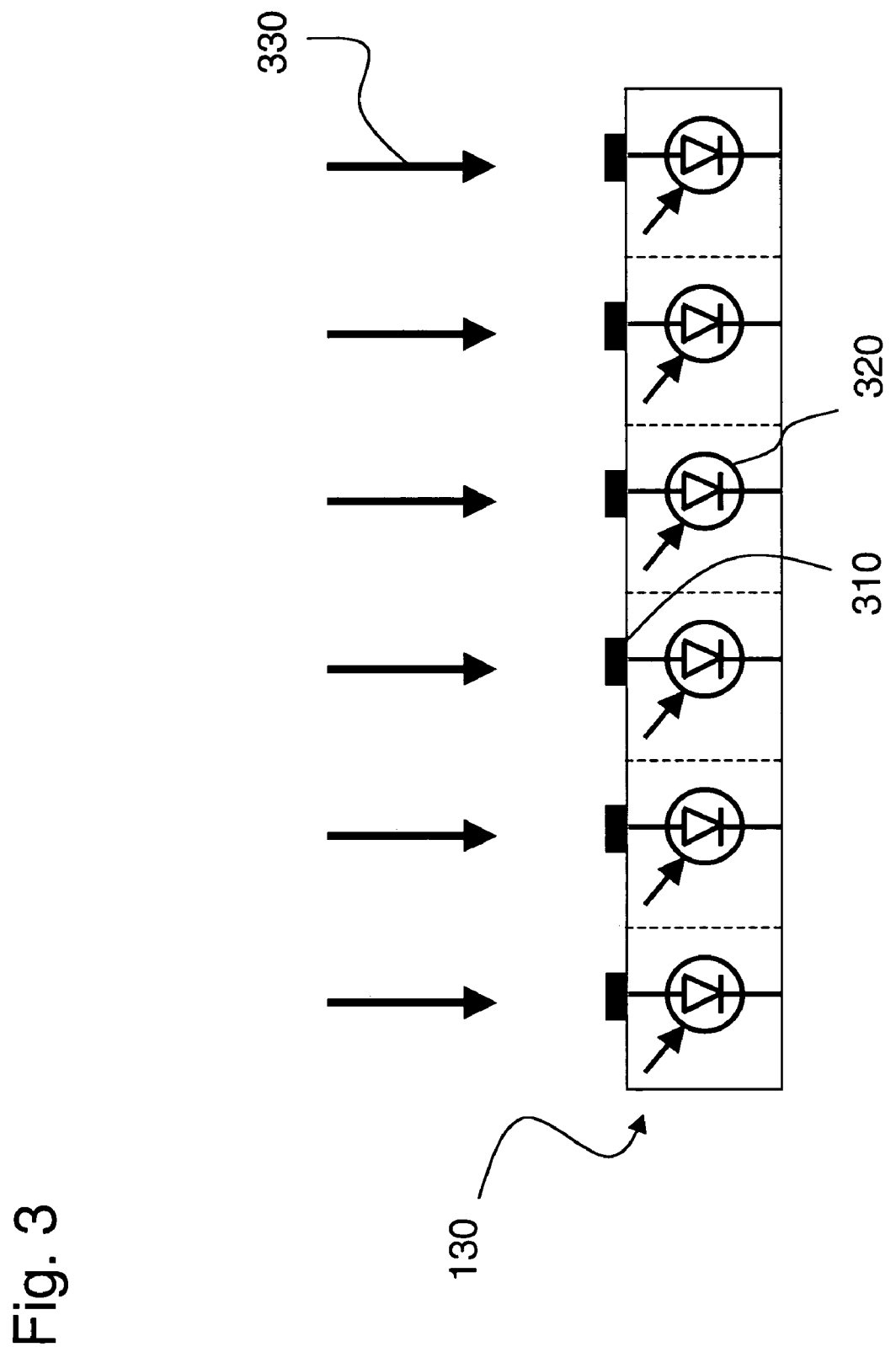
FIG. 3 shows a stimulating array according to the invention.

FIG. 3 schematically shows stimulating array 130 according to the invention. Stimulating array 130 includes a plurality of segments (separated by dotted lines on FIG. 3), where each segment has a photo-sensitive circuit 320 and an electrode 310 connected to the corresponding photo-sensitive circuit 320. The segments of stimulating array 130 are also referred to as pixels. Electrodes 310 are disposed in proximity to retinal neural cells (not shown on FIG. 3). Photo-sensitive circuit 320 receives image light 330 (i.e., light from an image formed by the eye at retina 120) and drives the corresponding electrode 310, which in turn stimulates a retinal neural cell (or cells) in proximity to electrode 310.

FIG. 3 illustrates positioning electrodes 310 on the upper side of the implant, i.e. on the side of illumination. This arrangement is suitable for a sub-retinal implant, when the light reaches the implant through the retina. For an epi-retinal implant, where the implant is on top of the retina, the electrodes are preferably positioned on the side opposite to the illuminated surface.

Although the invention may be practiced with various stimulating arrays 130 which are generally described in connection with FIG. 3, it is preferable to reduce the power required by stimulating array 130 because of the limited power available from ambient light.

Figure 4:
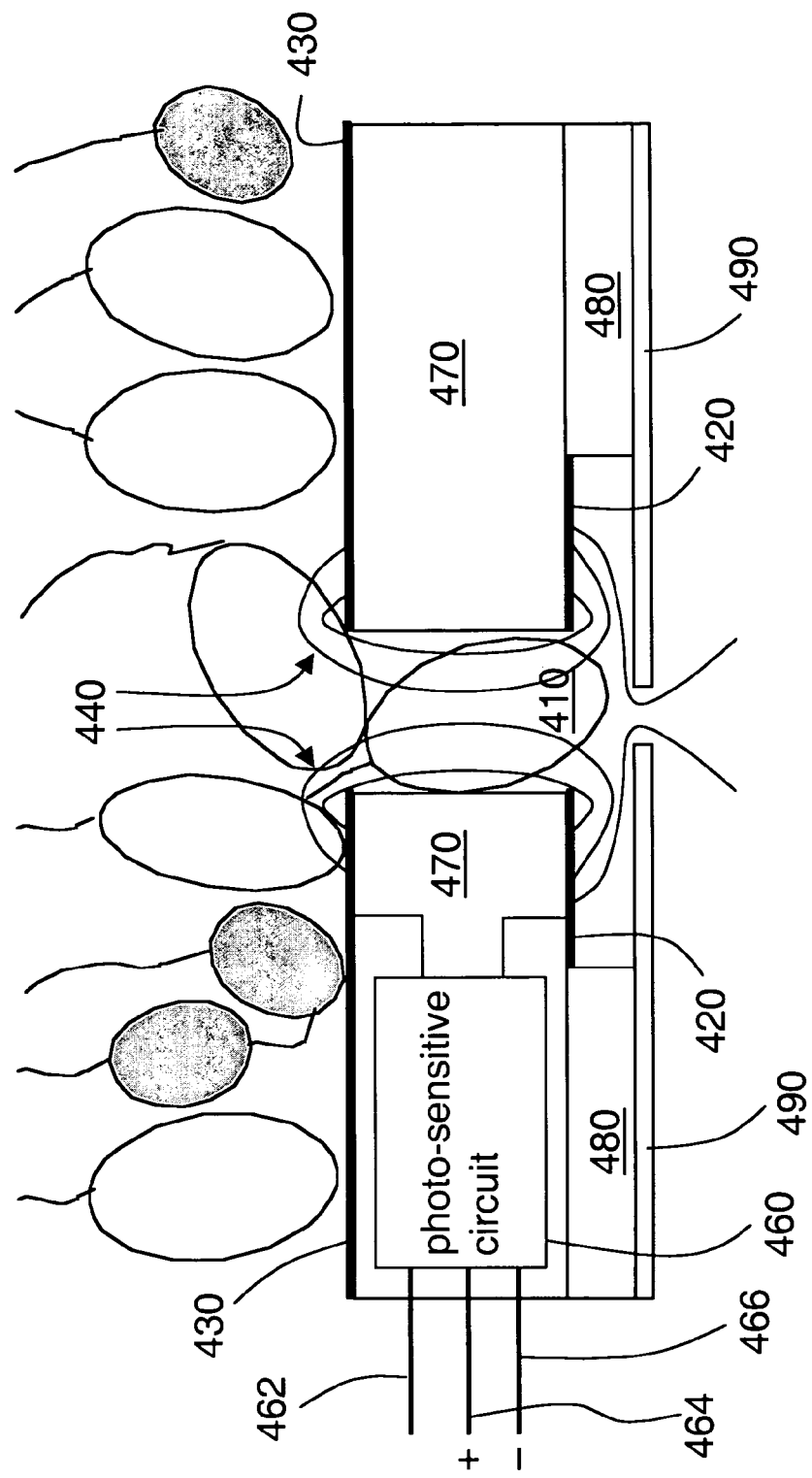
FIG. 4 shows a segment of a preferred stimulating array according to the invention.

Accordingly, FIG. 4 shows a segment of a preferred stimulating array 130. The segment of FIG. 4 includes an addressable electrode 420 and a common electrode 430 separated by a wafer 470. Common electrode 430 is the same for all segments of preferred stimulating array 130. Electric field 440 is shown across cell 410 which has migrated into a hole in wafer 470. Such migration is a natural physiological response of cells and may depend on the presence of nutrients for these cells, morphology of the implant surfaces and/or the size of the hole in wafer 470. Optionally, a growth (or inhibition) factor could be included to enhance (or decrease) the migration or growth of the neural cells. Suitable such factors include but are not limited to: BDNF (brain-derived neurotrophic factor, CNTF (ciliary neurotrophic factor), Forskolin, Laminin, N-CAM and modified N-CAMs.

A photo-sensitive circuit 460, fabricated in wafer 470, is connected to electrodes 420 and 430. A spacer layer 480 surrounds addressable electrode 420 laterally, and has a hole aligned with the hole in wafer 470. Thus a channel is formed passing through both wafer 470 and spacer layer 480, within which electrode 420 is disposed. A stop layer 490 is attached to spacer layer 480, and serves to prevent uncontrolled migration of cell (or cells) 410 entirely through the structure. Accordingly, the aperture (or optionally apertures) in stop layer 490 are preferably less than about 5 microns in diameter, since diameters in this range are suitable for preventing such cell migration.

Circuit 460 provides pulsed excitation of cell 410, which reduces required electrical power. Pulsed excitation of cell 410 will be perceived as a continuous visual input provided the interval between pulses is short enough. This persistence of vision phenomenon is also exploited in standard television and video applications. Suitable pulse durations are between about 0.01 ms and about 10 ms, as known in the art, and suitable repetition rates are between about 25 Hz and about 80 Hz. Since cellular recovery time after stimulation is on the order of 10–20 ms, such a repetition rate is perceived as continuous or nearly continuous illumination. For a pulse duration of 1 ms and a pulse repetition rate of 25 Hz (a typical television or video repetition rate), the duty cycle is 0.025 and the power dissipated at the electrodes will be reduced by a factor of 40 compared to a continuous excitation mode. Adding this factor of 40 to the running examples shows that roughly 31,000 pixels can be powered in a pulsed mode with the configuration of FIG. 1, and roughly 760,000 pixels can be powered in a pulsed mode with the configuration of FIG. 2.

Preferably, a single trigger circuit powered by the intra-ocular photovoltaic cells will provide a pulsed trigger signal 462 to all photo-sensitive circuits 460, which then provide pulses to corresponding electrodes 420, which in turn provides pulsed stimulation to retinal neural cells 410 that is responsive to local light intensity. Such triggering is analogous to pulsed readout of a CCD array, which is known in the art.

If the trigger circuit is integrated with the photovoltaic cells, four electrical connections are made between the photovoltaic cells and stimulating array 130: power lines 464 and 466, trigger line 462 and a return line (not shown). The power lines and trigger line are connected with wires, while the return connection can be made through either a wire or conductive bodily tissue(s) and/or fluid(s). An alternative is to trigger using power lines 464 and 466, such that photosensitive circuits 460 only receive power during the duration of the trigger pulse. In this case, only power and return lines are needed between the photovoltaic cells and stimulating array 130.

In addition to reducing required power by using pulsed excitation of cells 410, the embodiment of FIG. 4 reduces required power by improving electrode geometry. Stop layer 490 is electrically insulating, and therefore tends to increase the impedance between electrode 420 and infinity. The impedance of electrode 420 is $R=\gamma L_1/(\pi D^2/4)=90$ k$\Omega$, assuming $L_1=D=10$ µm, where D is the channel diameter and $L_1$ is the length of the channel in layer 470. Since less power is required to drive high impedance electrodes, power consumption per pixel is reduced by a factor of approximately 4 compared to cases where the electrode impedance is 22 kΩ. Furthermore, electrodes 420 and 430 on FIG. 4 act roughly as a parallel plate capacitor, which means that in order to obtain 30 mV across cell 410 to depolarize it, only 30 mV potential difference between electrodes 420 and 430 is required. Accordingly, it is preferred for the thickness of wafer 470 to be on the order of the size of the body of cell 410, which is typically in a range of about 5 to 15 microns. In the previous examples which assume an essentially spherical electrode geometry, 45 mV at the electrode is required to obtain 100 mV across the cell. Since power scales as voltage squared, power consumption per pixel is reduced by a factor of roughly 2 in changing from a spherical electrode configuration to a parallel plate electrode configuration.

Thus for the embodiment of FIG. 4, 43 nW per pixel is required for continuous excitation and 1 nW per pixel is required for pulsed excitation as discussed in connection with FIG. 3. Photovoltaic cells 110 as shown on FIG. 1 can provide power for pulsed excitation of about 250,000 pixels using only ambient light. As indicated above, positioning of a photovoltaic cell in the anterior chamber of the eye can increase this number by roughly a factor of 25, to 6 million pixels.

For chronic implantation of an electrode it is preferable to ensure that no electrochemical reactions take place at the electrode-electrolyte interface, since such reactions can lead to accumulation of toxic chemicals in bodily fluids and erosion of the electrode. Such reactions can be caused either by a DC current or by charging/discharging the electric double layer formed at the interface. A typical capacitance for an electric double layer is 10–20 $\mu F/cm^2$.

Accordingly, there are two conditions on the preferred electrode excitation: 1) there should be no net DC current supplied to the electrode, and 2) pulse durations should be comparable to or less than the time constant of the double layer. Condition 1 can be met by driving the electrodes with biphasic charge-balanced pulses. Since each biphasic pulse transfers no net charge, a succession of biphasic pulses gives zero DC current. The consequences of condition 2 can be appreciated by example. Suppose electrode 420 on FIG. 4 has an inside diameter of 10 μm and an outside diameter of 20 μm, giving a surface area of 236 $\mu m^2$. Assuming a double layer capacitance of 10 $\mu F/cm^2$, the double layer capacity of this electrode is 24 pF. The RC time constant of a 24 pF capacitor combined with a 90 kΩ resistor is about 2 μs, which is much shorter than the minimum pulse duration required for neural cell stimulation, which is on the order of a millisecond. Thus, in this example, pulses long enough to stimulate neural cells will cause electrochemical reactions at electrodes 420.

To avoid such electrochemical complications, it is preferable to increase the double layer capacitance of electrode 420 (and of electrode 430 as well, if necessary) to provide a time constant on the order of a cell excitation pulse duration. To accomplish this, electrode 420 (and optionally electrode 430) can be coated with a material having a high surface area. For example, carbon black has a surface area of about 1000 $m^2/g$ and is a suitable coating material for increasing double layer capacitance. Other suitable materials for such a coating include platinum black, iridium oxide, and silver chloride. For a surface area of 236 $\mu m^2$ a carbon black coating of 0.5 μm in thickness, assuming a density of roughly 1 $g/cm^3$ for carbon black, will provide adequate area to achieve a capacity of 11 nF in the double layer. The time constant is thereby increased to roughly 1 ms, so biphasic current pulses with positive and negative excursions on the order of 1 ms in duration will not cause undesired electrochemical reactions.

Figure 5:
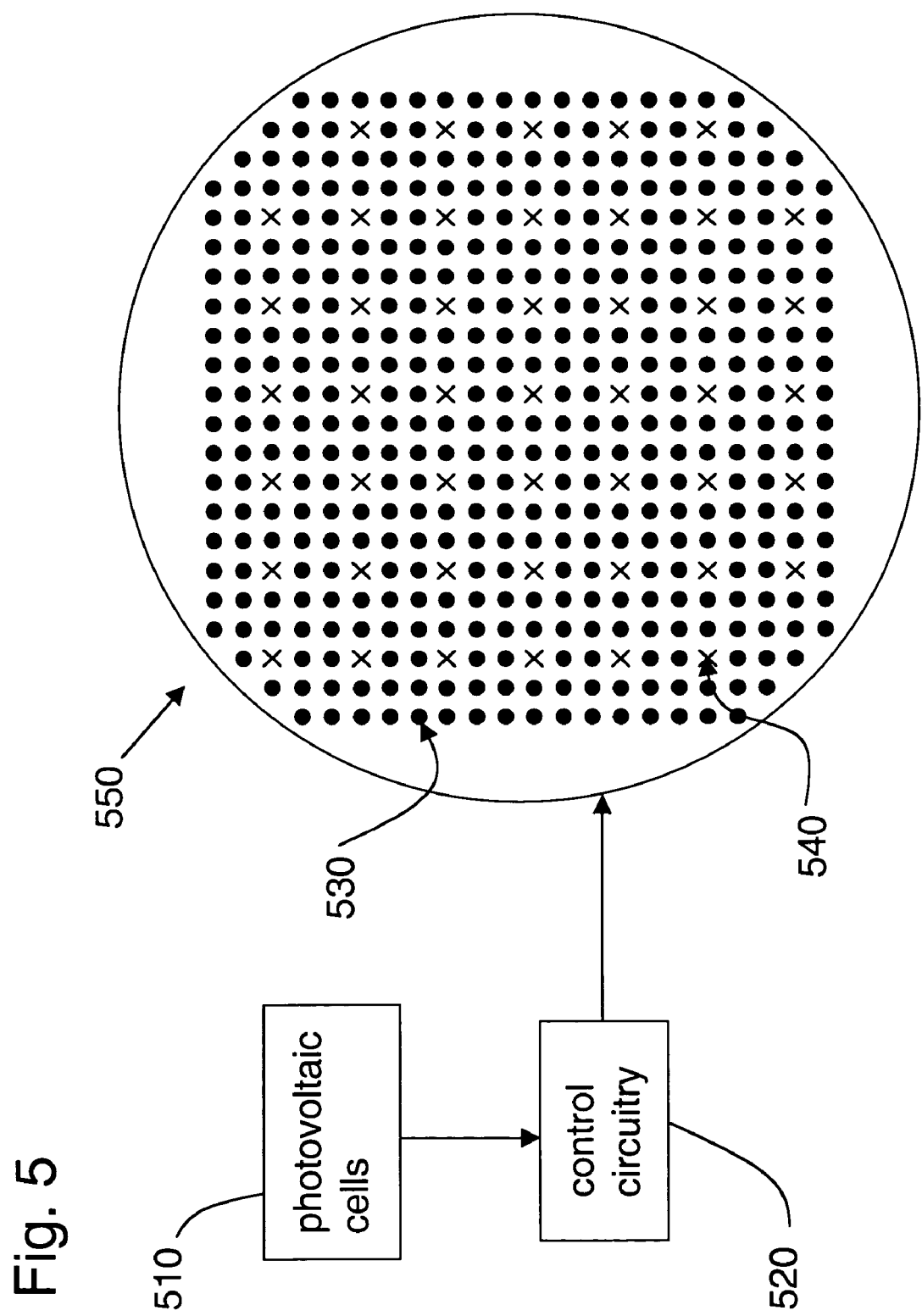
FIG. 5 shows an embodiment of the invention providing adaptation to varying ambient light level.

FIG. 5 shows an embodiment of the invention which provides adaptation to varying ambient light levels. Since available power from ambient light can vary by many orders of magnitude, and a substantially fixed amount of power is required for each pixel, adaptation to varying ambient light level entails varying the number of pixels that are energized. A stimulating array 550 is shown on FIG. 5 in a schematic top view (i.e., a view as seen looking into the eye at stimulating array 550). Stimulating array 550 includes a pixel subarray 530 (each pixel shown as a black circle) and a pixel subarray 540 (each pixel shown as an "X"). Intraocular photovoltaic cells 510 are connected to and provide electrical power to control circuitry 520. Control circuitry 520 selects which pixel subarrays to energize, depending on how much power is available from photovoltaic cells 510. For example, if a relatively large amount of power is available, subarrays 530 and 540 are both energized (or, alternatively, subarray 530 alone is energized), while if a relatively small amount of power is available, only subarray 540 is energized. A suitable method for selecting which subarray or subarrays to energize is to maximize the number of excited pixels subject to the constraint that the power per excited pixel not fall below a predetermined value.

In the example of FIG. 5, it is preferable for the smaller subarray (i.e., subarray 540) to be distributed substantially uniformly within the larger subarray (i.e., subarray 530) as shown on FIG. 5. With this arrangement, resolution is decreased as ambient light level decreases. If subarray 540 is positioned within a small fraction of the area of stimulating array 550, then the field of view decreases as ambient light level decreases, which is not preferred. Preferably, control circuitry 520 is integrated with stimulating array 550 into a single unit. For example, control circuitry 520 can be located on the periphery of stimulating array 550. For simplicity, the example of FIG. 5 shows only two pixel subarrays, but any number of pixel subarrays can be used to practice the invention. The number of pixels in each subarray can differ by factors of about 10, or can differ by any other convenient factor.

Recall, in the embodiment of FIG. 4, about 250,000 pixels can be powered by photovoltaic cells as shown on FIG. 1, while about 6 million pixels can be powered by a photovoltaic cell in the anterior chamber of the eye. These estimates assume an ambient power flux on the retina of about 0.9 $\mu W/mm^2$ (i.e., outdoors on a sunny day). However, provision of significant visual functionality does not require so many pixels. For example, to provide a visual acuity of 20/80, about 2500 pixels/$mm^2$ are required, while 20/200 visual acuity requires about 400 pixels/$mm^2$. An implant having a diameter of 3 mm will provide about a 10 degree visual field of view, so about 18000 pixels are required to provide 20/80 vision within a 10 degree field of view, and about 3000 pixels are required to provide 20/200 vision within a 10 degree field of view.

Thus, it can be seen that the embodiment of FIG. 5 can provide significant vision under reduced ambient lighting conditions (i.e., significantly less ambient light than outdoor daylight). Furthermore, visual acuity and/or field of view can increase as ambient light increases.

What is claimed is:

1. A retinal prosthesis, comprising:
 a) one or more photovoltaic cells adapted to be disposed within an eye and illuminated only with ambient light; and
 b) a stimulating array adapted to be disposed in proximity to a retina of said eye and receiving electrical power from said photovoltaic cells, said array including a plurality of segments each comprising:
  i) an electrode to stimulate one or more neural cells in proximity to said electrode; and
  ii) a photo-sensitive electrical circuit providing stimulation of said electrode responsive to image light received by said stimulating array;
 wherein said stimulating array comprises a plurality of subarrays of said segments and further comprising circuitry to select one or more of said subarrays to energize, based on a level of said ambient light.

2. The retinal prosthesis of claim 1, wherein said photovoltaic cells are adapted to be disposed in proximity to said retina.

3. The retinal prosthesis of claim 2, wherein said photovoltaic cells are adapted to be disposed away from a macula of said retina.

4. The retinal prosthesis of claim 3, wherein said photovoltaic cells are spaced apart to permit peripheral vision in parts of said retina not blocked by said photovoltaic cells.

5. The retinal prosthesis of claim 1, wherein said photovoltaic cells are adapted to be disposed in an anterior chamber of said eye.

6. The retinal prosthesis of claim 5, wherein said photovoltaic cells are adapted to be disposed in front of an iris of said eye.

7. The retinal prosthesis of claim 1, wherein said stimulation is pulsed stimulation.

8. The retinal prosthesis of claim 7, wherein said pulsed stimulation is biphasic pulsed stimulation.

9. The retinal prosthesis of claim 1, further comprising a coating of a high surface area material deposited on said electrodes, whereby double layer capacitance of said electrodes is increased.

10. The retinal prosthesis of claim 9, wherein said material comprises carbon black, platinum black, iridium oxide or silver chloride.

11. The retinal prosthesis of claim 1, wherein each of said segments further comprises a channel within which said electrode is disposed, said channels disposed to facilitate migration of neural cells of said retina into said channels.

12. The retinal prosthesis of claim 1, wherein said plurality of segments has at least 3000 segments.

13. A method for stimulating a retina, comprising:
 a) illuminating one or more photovoltaic cells within an eye with only ambient light to provide electrical power;
 b) energizing a stimulating array in proximity to said retina of said eye with said electrical power, said array including a plurality of segments each comprising an electrode and a photo-sensitive electrical circuit connected to said electrode;
 c) receiving image light with said stimulating array; and
 d) stimulating one or more neural cells in proximity to said electrodes responsive to said received image light;
 wherein said stimulating array comprises a plurality of subarrays of said segments and further comprising selecting one or more of said subarrays to energize, based on a level of said ambient light.

14. The method of claim 13, wherein said stimulating comprises pulsed stimulating.

15. The method of claim 14, wherein said pulsed stimulating comprises biphasic pulsed stimulating.

16. The method of claim 13, wherein said selecting comprises maximizing a number of energized segments subject to a constraint that said electrical power divided by said number be above a predetermined value.

17. The method of claim 13, wherein each of said segments further comprises a channel within which said electrode is disposed.

18. The method of claim 17, further comprising allowing neural cells of said retina to migrate into said channels.

19. The method of claim 17, further comprising inducing neural cells of said retina to migrate into said channels.

* * * * *